United States Patent
Chen et al.

(10) Patent No.: US 11,820,750 B2
(45) Date of Patent: Nov. 21, 2023

(54) **HIGH EFFICIENT SEX PHEROMONE LURES FOR *ECTROPIS OBLIQUE* AND *ECTROPIS GRISESCENS***

(71) Applicant: CHANGZHOU UNIVERSITY, Jiangsu (CN)

(72) Inventors: Xin Chen, Changzhou (CN); Ke Chen, Changzhou (CN); Xueyuan Zhang, Changzhou (CN); Chengfang Zhang, Changzhou (CN); Jianlong Bi, Changzhou (CN); Yanqiang Jin, Changzhou (CN); Mingwei Shan, Changzhou (CN); Shuai Zhao, Changzhou (CN); Mingcheng Qian, Changzhou (CN)

(73) Assignee: CHANGZHOU UNIVERSITY, Changzhou (CN)

(*) Notice: Subject to any disclaimer, the term of this patent is extended or adjusted under 35 U.S.C. 154(b) by 0 days.

(21) Appl. No.: 18/173,037

(22) Filed: Feb. 22, 2023

(65) Prior Publication Data
US 2023/0202995 A1  Jun. 29, 2023

Related U.S. Application Data

(63) Continuation of application No. PCT/CN2021/117902, filed on Sep. 13, 2021.

(30) Foreign Application Priority Data

Aug. 17, 2021 (CN) .......................... 202110941562.6

(51) Int. Cl.
*C07D 303/04* (2006.01)
*A01N 43/20* (2006.01)

(52) U.S. Cl.
CPC ........... *C07D 303/04* (2013.01); *A01N 43/20* (2013.01)

(58) Field of Classification Search
CPC ........ C07D 303/04; A01M 1/02; A01N 27/00; A01N 43/20
See application file for complete search history.

(56) References Cited

FOREIGN PATENT DOCUMENTS

| CN | 102125036 A | | 7/2011 | |
|---|---|---|---|---|
| CN | 105685041 A | | 6/2016 | |
| CN | 105815317 A | | 8/2016 | |
| CN | 106035332 A | | 10/2016 | |
| CN | 106689133 A | | 5/2017 | |
| CN | 105815317 B | * | 3/2019 | ............. A01N 27/00 |
| CN | 110476971 A | | 11/2019 | |
| CN | 110859180 A | | 3/2020 | |
| CN | 111406744 A | | 7/2020 | |
| CN | 111406744 B | * | 6/2021 | ............. A01N 27/00 |

OTHER PUBLICATIONS

Xu, Kai et al., Total Synthesis of (3Z,9Z,6S,7R) and (3Z,9Z,6R,7S)-6,7-epoxy-3,9-octadecadienes, Synthetic Communications, 2017, 6 pages.
Li, Xiwang et al., Research Progress and Prospect of Green Control Techniques of Ectropis obliqua, Journal of Tea Science, 37(4): 325-331, 2017.
First Office Action in Chinese Application No. 202110941562.6 dated Mar. 2, 2022, 12 pages.
Decision to grant a patent in Chinese Application No. 202110941562.6 dated Aug. 10, 2022, 3 pages.
International Search Report in PCT/CN2021/117902 dated May 13, 2022, 6 pages.
Written Opinion in PCT/CN2021/117902 dated May 13, 2022, 5 pages.

* cited by examiner

*Primary Examiner* — Amanda L. Aguirre
(74) *Attorney, Agent, or Firm* — METIS IP LLC

(57) ABSTRACT

The present disclosure generally relates to the field of biological control of *Ectropis. oblique* and *Ectropis grisescens* as pests in tea plantations, and in particular to a high efficient sex pheromone lures for *E. oblique* and *E. grisescens*. By combining (3Z,6Z,9Z)-octadecatriene with two different configurations of (3Z,9Z)-6,7-epoxy-octadecadiene and (3Z,6Z)-9,10-epoxy-octadecadiene, high efficient sex pheromone lures were obtained. The high efficient sex pheromone lures have significantly improved trapping effect on *E. oblique* and *E. grisescens*.

2 Claims, 1 Drawing Sheet

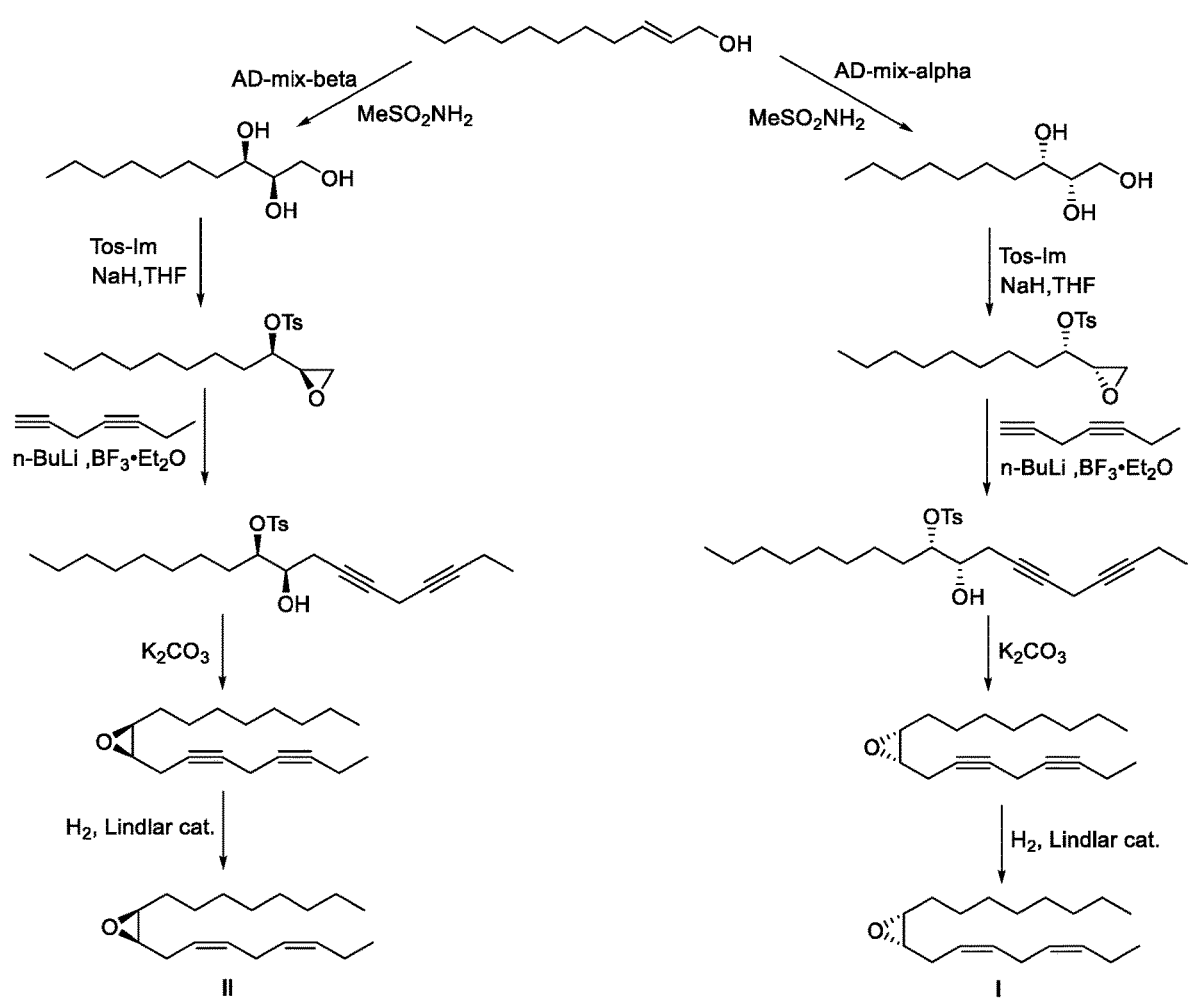

HIGH EFFICIENT SEX PHEROMONE LURES FOR *ECTROPIS OBLIQUE* AND *ECTROPIS GRISESCENS*

CROSS-REFERENCE TO RELATED APPLICATIONS

This application is Continuation of International Application No. PCT/CN2021/117902 filed on Sep. 13, 2021, which claims priority of Chinese Patent Application No. 202110941562.6, filed on Aug. 17, 2021, the entire contents of which are incorporated herein by reference.

TECHNICAL FIELD

The present disclosure generally relates to the field of control of *Ectropis oblique* and *Ectropis grisescens*, and in particular to a high efficient sex pheromone lure for *E. oblique* and *E. grisescens*.

BACKGROUND

*E. oblique* (also referred to as *Ectropis oblique*, *Ectropis oblique* Prout) and *E. grisescens* (also referred to as *Ectropis grisescens*, *Ectropis grisescens* Warren) belonging to Lepidoptera, Geometridae, are the main pests of tea trees in China. Their larvae bit the edges of tender tea leaves, forming reticular translucent membrane spots, while the older larvae bit the tea leaves, forming a "C"-shaped notch. Seriously, the new leaves and mature leaves of the tea plants are eaten, leaving only the bare branches, which looks like being burned, having a great impact on tea production. *E. oblique* and *E. grisescens* are closely related species, therefore, they are very similar in shape, have the overlap in occurrence area and time, and have the same host plant. In order to better ensure the pollution-free organic planting of tea, non-toxic and environmentally friendly technologies, such as physical and biological prevention and control, are gradually replacing traditional pesticides.

The use of insect sex pheromones to control the tea pests is an efficient, specific, and environmentally friendly biological control technology. There are many research reports on the identification and synthesis of sex pheromones of *E. oblique*. In 1994, Liu Tianlin and others initially confirmed that two important components of sex pheromones of *E. oblique* are (3Z,6Z,9Z)-octadecatriene and (3Z,9Z)-6,7-epoxyoctadecadiene (Liu Tianlin, Li Zhengming, Luo Zhiqiang, et al. Synthesis of several active components of the sex pheromone of *E. oblique*. Journal of Nankai University (Natural Science Edition). 1994: 82-86). In 2017, Wan Xiaochun's research group (J. Yu, F. Guo, Y Q Yang, et al. Synthesis of the enantiomers of (3Z,9Z)-cis-6,7-epoxy-3,9-octadecadiene, one of the major components of the sex pheromone of *Ectropis oblique* Prout. Tetrahedron Asymmetry. 2017, 28: 758-761) and Xin Chen's research group (K. Xu, S. Zhao, J K Xu, et al. Total synthesis of (3Z,9Z, 6S,7R) and (3Z,9Z,6R,7S)-6,7-epoxy-3,9-octadecadienes. Synth. Commun. 2017, 47: 1848-1853) synthesized (3Z,9Z, 6S,7R)-6,7-epoxy-octadecadiene and (3Z,9Z,6R,7S)-6,7-epoxy-octadecadiene by different routes, but the effect of field trapping experiments with the synthesized components was not obvious. Zongmao Chen group (Z. Luo, F. H. Magsi, Z. Li, et al. Development and evaluation of sex Pheromone mass trapping technology for *Ectropis grisescens*: A potential integrated pest management strategy. Insects, 2020, 11: 15) reported that two compounds, (3Z,6Z,9Z)-octadecatriene and (3Z,9Z)-cis-6,7-epoxy-octadecadiene, at a ratio of 30:70 and impregnated into rubber septa at 1 mg, were very attractive to male moths of *E. grisescens*. In another report (Z. X. Luo, Z. Q. Li, X. M. Cai, et al. Evidence of premating isolation between two sibling moths: *Ectropis grisescens* and *Ectropis obliqua* (Lepidoptera: Geometridae). J. Econom. Entomol. 2017, 110: 2364-2370), the same group stated that (3Z,6Z,9Z)-octadecatriene and (3Z,9Z)-cis-6,7-epoxy-octadecadiene were sex pheromone components of *E. grisescens*, whereas (3Z,6Z,9Z)-octadecatriene, (3Z,9Z)-cis-6,7-epoxy-octadecadiene and (3Z,9Z)-cis-6,7-epoxy-nonadecadiene were sex pheromone components of *E. obliqua*.

SUMMARY

The purpose of the present disclosure is to provide a high efficient sex pheromone lure for *E. oblique* and *E. grisescens*, and to provide a preparation method for synergistic components of the high efficient sex pheromone lure.

The inventors found that octadecadiene epoxides are one or more regioisomers, including 3,4-position, 6,7-position, and 9,10-position epoxides. In order to optimize trapping activity of a sex attractant for *E. oblique* and *E. grisescens*, a structure of the octadecadiene epoxides and a ratio of each regioisomer were studied in depth.

One of the embodiments in the present disclosure provides a high efficient sex pheromone lure for *E. oblique* and *E. grisescens*. The active ingredients of the sex pheromone lure may include (3Z,6Z,9Z)-octadecatriene and two octadecadiene epoxides. The sex pheromone lure, or sex pheromone attractant, may be used to trap *E. oblique* and *E. grisescens*. The sex pheromone lure may be used as an attracting core placed in a trap to trap *E. oblique* and *E. grisescens*.

In some embodiments, the octadecadiene epoxides are any two of (6Z,9Z)-3,4-epoxy-octadecadiene, (3Z,9Z)-6,7-epoxy-octadecadiene, or (3Z,6Z)-9,10-epoxy-octadecadiene.

In some embodiments, the (6Z,9Z)-3,4-epoxy-octadecadiene is (6Z,9Z,3S,4R)-3,4-epoxy-octadecadiene (abbreviated as (6Z,9Z-3S,4R)-epoxy-18:H) or (6Z,9Z,3R,4S)-3,4-epoxy-octadecadiene (abbreviated as (6Z,9Z-3R,4S)-epoxy-18:H) (see Formula 1).

In some embodiments, the (3Z,9Z)-6,7-epoxy-octadecadiene is (3Z,9Z,6S,7R)-6,7-epoxy-octadecadiene (abbreviated as (3Z,9Z-6S,7R)-epoxy-18:H) or (3Z,9Z,6R,7S)-6,7-epoxy-octadecadiene (abbreviated as (3Z,9Z-6R,7S)-epoxy-18:H). In some embodiments, the (3Z,9Z)-6,7-epoxy-octadecadiene is the (3Z,9Z,6S,7R)-6,7-epoxy-octadecadiene.

In some embodiments, the (3Z,6Z)-9,10-epoxy-octadecadiene is (3Z,6Z,9S,10R)-9,10-epoxy-octadecadiene (abbreviated as (3Z,6Z-9S,10R)-epoxy-18:H) or (3Z,6Z,9R,10S)-9,10-epoxy-octadecadiene (abbreviated as (3Z,6Z-9R,10S)-epoxy-18:H). In some embodiments, the (3Z,6Z)-9,10-epoxy-octadecadiene is the (3Z,6Z,9S,10R)-9,10-epoxy-octadecadiene.

In some embodiments, two octadecadiene epoxides are the (3Z,9Z)-6,7-epoxy-octadecadiene and the (3Z,6Z)-9,10-epoxy-octadecadiene.

In some embodiments, two octadecadiene epoxides are the (3Z,9Z,6S,7R)-6,7-epoxy-octadecadiene and the (3Z,6Z,9S,10R)-9,10-epoxy-octadecadiene.

In some embodiments, a weight ratio of the (3Z,9Z,6S,7R)-6,7-epoxy-octadecadiene to the (3Z,6Z,9S,10R)-9,10-epoxy-octadecadiene is 9:1-1:9.

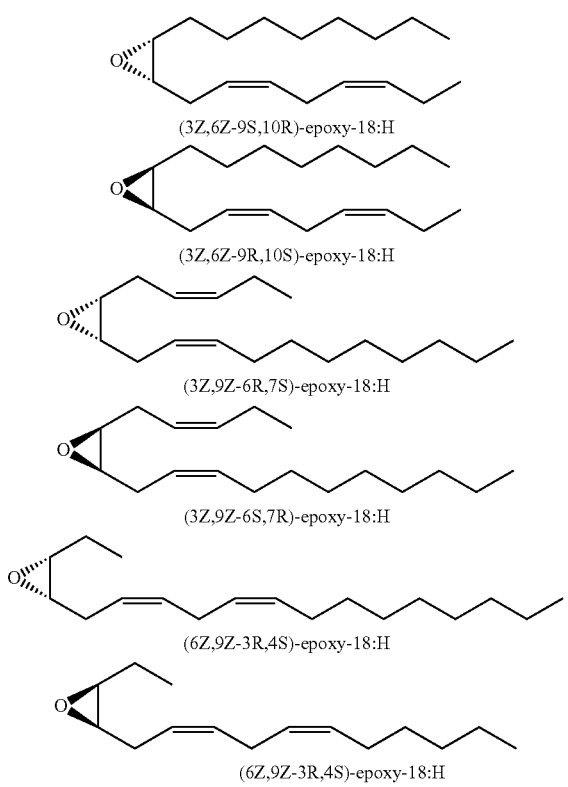

(3Z,6Z-9S,10R)-epoxy-18:H (3Z,6Z-9R,10S)-epoxy-18:H (3Z,9Z-6R,7S)-epoxy-18:H (3Z,9Z-6S,7R)-epoxy-18:H (6Z,9Z-3R,4S)-epoxy-18:H (6Z,9Z-3R,4S)-epoxy-18:H In some embodiments, the (3Z,6Z,9S,10R)-9,10-epoxy-octadecadiene ((3Z,6Z-9S,10R)-epoxy-18:H) (I) and the (3Z,6Z,9R,10S)-9,10-epoxy-octadecadiene ((3Z,6Z-9R,10S)-epoxy-18:H) (II) are used as the synergistic components of the high efficient sex pheromone lure for *E. oblique* and *E. grisescens*, and the synthetic route is shown in FIG. 1.

The beneficial effect of the present disclosure is that it is the first found that the (3Z,6Z)-9,10-epoxy-octadecadiene (e.g., (3Z,6Z,9S,10R)-9,10-epoxy-octadecadiene) has a synergistic effect on the trapping of *E. oblique* and *E. grisescens*, and the (3Z,9Z,6S,7R)-6,7-epoxy-octadecadiene compounded with the (3Z,6Z,9S,10R)-9,10-epoxy-octadecadiene has significantly improved the effect of trapping *E. oblique* and *E. grisescens*.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments.

FIG. 1 illustrates exemplary synthetic routes of the (3Z, 6Z-9S,10R)-epoxy-18:H (I) and the (3Z,6Z-9R,10S)-epoxy-18:H (II) according to some embodiments of the present disclosure.

DETAILED DESCRIPTION

The present disclosure will now be further described in conjunction with specific embodiments, and the following embodiments are intended to illustrate the present disclosure rather than limiting the present disclosure. As used in the disclosure and the appended claims, the singular forms "a," "an," and "the" include plural forms unless the content clearly dictates otherwise; the plural forms may be intended to include singular forms as well.

Synthesis of the Synergistic Ingredients of the High Efficient Sex Pheromone Lure Embodiment 1: Synthesis of the (3Z,6Z,9S,10R)-9,10-epoxy-octadecadiene (I)

Step 1: Synthesis of (2S,3S)-1,2,3-undecanetriol

AD-mix-alpha (41.2 g) was dissolved in a mixed solution of tert-butanol:water=1:1 (total 200 mL), and after the temperature of the above system was lowered to 0° C., methanesulfonamide (2.8 g, 29 mmoL) and trans-2-undecenol (5 g, 29 mmoL) were added and reacted for 3 days. The solution was monitored by thin layer chromatography (TLC), quenched by slowly adding $NaHSO_4$ (54 g) at 0° C., and suction filtered, the filtrate was extracted with ethyl acetate, spin-dried, and purified by column chromatography to obtain (2S,3S)-1,2,3-undecanetriol (4.5 g, 75% yield) as a white solid.

Step 2: Synthesis of (2S,3S)-1,2-epoxy-3-p-toluenesulfonate-undecane (2S,3S)-1,2,3-undecanetriol (4.4 g, 21.6 mmol) was dissolved in dry tetrahydrofuran (150 mL), the temperature of the system was lowered to 0° C., NaH (2.59 g, 64.8 mmoL) was slowly added, and after stirring for 30 minutes, Tos-Im (11.5 g, 51.8 mmoL) was added and reacted at room temperature for 4.5 hours. The solution was monitored by TLC, quenched by adding water (58 mL) at 0° C., the solvent was spin-dried, extracted with ethyl acetate, and purified by column chromatography to obtain the (2S,3S)-1,2-epoxy-3-p-toluenesulfonate-undecane (3 g, 41% yield) as a white solid.

Step 3: Synthesis of (9S,10R)-9,10-epoxy-octadeca-3,6-diyne 3,6-Heptadiyne (2.34 g, 25.4 mmoL) was added to the dried tetrahydrofuran (130 mL), the temperature of the system was lowered to −78° C., and n-butyllithium (10.3 mL, 25.4 mmol, 2.5 M in hexane) was added into the system dropwise under the protection of nitrogen to react for 15 minutes, boron trifluoride ether (2.4 g, 21.2 mmol) was added and reacted for 10 minutes, then (2S,3S)-1,2-epoxy-3-p-toluenesulfonate-undecane (2.9 g, 8.5 mmoL) was dissolved in tetrahydrofuran (20 mL), which was added dropwise to the system and reacted at −78° C. for 12 hours. The solution was monitored by TLC, quenched by adding saturated $NH_4Cl$ (20 mL), extracted with ethyl acetate, spin-dried with the organic phase, methanol (40 mL) was added, $K_2CO_3$ (4.64 g, 33.1 mmoL) was added at 0° C. After the reaction was completed, methanol was spin-dried, the solute was extracted with ethyl acetate, the solvent was spin-dried, column chromatography was used for purification to obtain (9S,10R)-9,10-epoxy-octadeca-3,6-diyne (0.54 g, yield 25%) as an oily liquid.

Step 4: Synthesis of (3Z,6Z,9S,10R)-9,10-epoxy-octadecadiene (I)

n-hexane (15 mL) and Lindlar catalyst (32 mg) were added to a 100 mL round-bottom flask, and hydrogen was introduced to replace the gas in the round-bottom flask for 3 times, (9S,10R)-9,10-epoxy-octadeca-3,6-diyne (0.32 g, 1.2 mmol) was added and reacted under hydrogen for 5 hours. The reaction was monitored by TLC, and the reaction mixture was suction filtered through a silica gel pad, the filter cake was washed with ethyl acetate, the filtrate was spin-dried, and column chromatography was used for purification to obtain (3Z,6Z,9S,10R)-9,10-epoxy-octadecadiene (124 mg, 38% yield) as a yellow oily liquid. $^1$H NMR (500 MHz, CDCl$_3$) δ: 5.27-5.54 (m, 4H), 2.91-2.95 (m, 2H), 2.80 (t, J=7.0 Hz, 2H), 2.36-2.43 (m, 1H), 2.19-2.25 (m, 1H), 2.03-2.11 (m, 2H), 1.47-1.54 (m, 2H), 1.27-1.45 (m, 12H), 0.97 (t, J=7.5 Hz, 3H), 0.88 (t, J=6.5 Hz, 3H); $^{13}$C NMR (125 MHz, CDCl$_3$) δ: 132.5, 130.9, 126.7, 124.3, 57.2, 56.6, 32.0, 29.6, 29.7, 29.4, 27.9, 26.8, 26.4, 25.8, 22.8, 20.7, 14.4, 14.2; MS (ESI): m/z 287 [M+Na]$^+$.

Embodiment 2: Synthesis of
(3Z,6Z,9R,10S)-9,10-epoxy-octadecadiene (II)

The synthesis method is the same as that in Embodiment 1, except that the catalyst is replaced by AD-mix-beta in the Sharpless asymmetric dihydroxylation reaction step.

The spectral data of the obtained (3Z,6Z,9R,10S)-9,10-epoxy-octadecadiene are as follows: $^1$H NMR (500 MHz, CDCl$_3$) δ: 5.27-5.55 (m, 4H), 2.91-2.96 (m, 2H), 2.80 (t, J=7.0 Hz, 2H), 2.38-2.43 (m, 1H), 2.19-2.25 (m, 1H), 2.04-2.10 (m, 2H), 1.42-1.58 (m, 2H), 1.25-1.37 (m, 12H), 0.97 (t, J=7.5 Hz, 3H), 0.88 (t, J=6.7 Hz, 3H); $^{13}$C NMR (125 MHz, CDCl$_3$) δ: 132.5, 130.9, 126.7, 124.4, 57.5, 56.6, 32.0, 29.7, 29.6, 29.4, 27.9, 26.8, 26.4, 25.8, 22.8, 20.8, 14.4, 14.3; MS (ESI): m/z 282 [M+NH$_4$]$^+$.

Trapping Tests of *E. oblique* and *E. grisescens* with the High Efficient Sex Pheromone Lures (1) Screening of a Single Octadecadiene Epoxide Embodiment 3: 1.25 mg (3Z,6Z,9Z)-octadecatriene and 3.75 mg (6Z,9Z,3S,4R)-3,4-epoxy-octadecadiene were dissolved in n-hexane, the obtained solution was added dropwise into a slow-release carrier (i.e., rubber septum), and after the solvent was volatilized, the sex pheromone lure was obtained.

Embodiment 4: 1.25 mg (3Z,6Z,9Z)-octadecatriene and 3.75 mg (6Z,9Z,3R,4S)-3,4-epoxy-octadecadiene were dissolved in n-hexane, the obtained solution was added dropwise into a rubber septum, and after the solvent was volatilized, the sex pheromone lure was obtained.

Embodiment 5: 1.25 mg (3Z,6Z,9Z)-octadecatriene and 3.75 mg (3Z,9Z,6S,7R)-6,7-epoxy-octadecadiene were dissolved in n-hexane, the obtained solution was added dropwise into a rubber septum, and after the solvent was volatilized, the sex pheromone lure was obtained.

Embodiment 6: 1.25 mg (3Z,6Z,9Z)-octadecatriene and 3.75 mg (3Z,9Z,6R,7S)-6,7-epoxy-octadecadiene were dissolved in n-hexane, the obtained solution was added dropwise into a rubber septum, and after the solvent was volatilized, the sex pheromone lure was obtained.

Embodiment 7: 1.25 mg (3Z,6Z,9Z)-octadecatriene and 3.75 mg (3Z,6Z,9S,10R)-9,10-epoxy-octadecadiene were dissolved in n-hexane, the obtained solution was added dropwise into a rubber septum, and after the solvent was volatilized, the sex pheromone lure was obtained.

Embodiment 8: 1.25 mg (3Z,6Z,9Z)-octadecatriene and 3.75 mg (3Z,6Z,9R,10S)-9,10-epoxy-octadecadiene were dissolved in n-hexane, the obtained solution was added dropwise into a rubber septum, and after the solvent was volatilized, the sex pheromone lure was obtained.

Embodiment 9: Field trapping tests were carried out at a tea plantation of Jintan Xinpin Tea Industry Co., Ltd., Changzhou City, Jiangsu Province. Sex pheromone lures used in the tests were made according to the schemes described in Embodiments 3-8, and a blank control was a lure made of n-hexane. The sex pheromone lure was used with a trap, each treatment process was repeated 3 times, and the number of trapped male pests in one month was counted. The trapping results of the sex pheromone lures based on Embodiments 3-8 are shown in Table 1.

TABLE 1

| | Trapping results of *E. oblique* | |
|---|---|---|
| Treatment | Total number of trapped *E. oblique* (Head) | Average number of trapped *E. oblique* (Head/Trap) |
| Blank control | 0 | 0 |
| Embodiment 3 | 0 | 0 |
| Embodiment 4 | 0 | 0 |
| Embodiment 5 | 10 | 3.3 |
| Embodiment 6 | 9 | 3 |
| Embodiment 7 | 0 | 0 |
| Embodiment 8 | 0 | 0 |

The results showed that the trapping effects of the octadecadiene epoxides with different configurations on the *E. oblique* (e.g., male *E. oblique*) are significantly different.

(3Z,9Z,6S,7R)-6,7-epoxy-octadecadiene and (3Z,9Z,6R,7S)-6,7-epoxy-octadecadiene has certain trapping capacity, while (6Z,9Z,3R,4S)-3,4-epoxy-octadecadiene, (6Z,9Z,3S,4R)-3,4-epoxy-octadecadiene, (3Z,6Z,9S,10R)-9,10-epoxy-octadecadiene, (3Z,6Z,9R,10S)-9,10-epoxy-octadecadiene have no trapping effect at all.

(2) Screening of Binary Octadecadiene Epoxides: A Combination of (3Z,9Z)-6,7-epoxy-octadecadiene and (3Z,6Z)-9,10-epoxy-octadecadiene Embodiment 10: 1.25 mg (3Z,6Z,9Z)-octadecatriene, 3.375 mg (3Z,9Z,6S,7R)-6,7-epoxy-octadecadiene and 0.375 mg (3Z,6Z,9S,10R)-9,10-epoxy-octadecadiene were dissolved in n-hexane, the obtained solution was added dropwise to a rubber septum, and after the solvent was volatilized, the sex pheromone lure was obtained.

Embodiment 11: 1.25 mg (3Z,6Z,9Z)-octadecatriene, 3.125 mg (3Z,9Z,6S,7R)-6,7-epoxy-octadecadiene and 0.625 mg (3Z,6Z,9S,10R)-9,10-epoxy-octadecadiene were dissolved in n-hexane, the obtained solution was added dropwise to a rubber septum, and after the solvent was volatilized, the sex pheromone lure was obtained.

Embodiment 12: 1.25 mg (3Z,6Z,9Z)-octadecatriene, 2.5 mg (3Z,9Z,6S,7R)-6,7-epoxy-octadecadiene and 1.25 mg (3Z,6Z,9S,10R)-9,10-epoxy-octadecadiene were dissolved in n-hexane, the obtained solution was added dropwise to a rubber septum, and after the solvent (n-hexane) was volatilized, the sex pheromone lure was obtained.

Embodiment 13: 1.25 mg (3Z,6Z,9Z)-octadecatriene, 1.875 mg (3Z,9Z,6S,7R)-6,7-epoxy-octadecadiene and 1.875 mg (3Z,6Z,9S,10R)-9,10-epoxy-octadecadiene were dissolved in n-hexane, the obtained solution was added dropwise to a rubber septum, and after the solvent was volatilized, the sex pheromone lure was obtained.

Embodiment 14: 1.25 mg (3Z,6Z,9Z)-octadecatriene, 1.25 mg (3Z,9Z,6S,7R)-6,7-epoxy-octadecadiene and 2.5 mg (3Z,6Z,9S,10R)-9,10-epoxy-octadecadiene were dissolved in n-hexane, the obtained solution was added dropwise to a rubber septum, and after the solvent was volatilized, the sex pheromone lure was obtained.

Embodiment 15: 1.25 mg (3Z,6Z,9Z)-octadecatriene, 0.625 mg (3Z,9Z,6S,7R)-6,7-epoxy-octadecadiene and 3.125 mg (3Z,6Z,9S,10R)-9,10-epoxy-octadecadiene were dissolved in n-hexane, the obtained solution was added dropwise to a rubber septum, and after the solvent was volatilized, the sex pheromone lure was obtained.

Embodiment 16: 1.25 mg (3Z,6Z,9Z)-octadecatriene, 0.375 mg (3Z,9Z,6S,7R)-6,7-epoxy-octadecadiene and 3.375 mg (3Z,6Z,9S,10R)-9,10-epoxy-octadecadiene were dissolved in n-hexane, the obtained solution was added dropwise to a rubber septum, and after the solvent was volatilized, the sex pheromone lure was obtained.

Embodiment 17: 1.25 mg (3Z,6Z,9Z)-octadecatriene, 3.375 mg (3Z,9Z,6S,7R)-6,7-epoxy-octadecadiene and 0.375 mg (3Z,6Z,9R,10S)-9,10-epoxy-octadecadiene were dissolved in n-hexane, the obtained solution was added dropwise to a rubber septum, and after the solvent was volatilized, the sex pheromone lure was obtained.

Embodiment 18: 1.25 mg (3Z,6Z,9Z)-octadecatriene, 1.875 mg (3Z,9Z,6S,7R)-6,7-epoxy-octadecadiene and 1.875 mg (3Z,6Z,9R,10S)-9,10-epoxy-octadecadiene were dissolved in n-hexane, the obtained solution was added dropwise to a rubber septum, and after the solvent was volatilized, the sex pheromone lure was obtained.

Embodiment 19: 1.25 mg (3Z,6Z,9Z)-octadecatriene, 0.375 mg (3Z,9Z,6S,7R)-6,7-epoxy-octadecadiene and 3.375 mg (3Z,6Z,9R,10S)-9,10-epoxy-octadecadiene were dissolved in n-hexane, the obtained solution was added dropwise to a rubber septum, and after the solvent was volatilized, the sex pheromone lure was obtained.

Embodiment 20: 1.25 mg (3Z,6Z,9Z)-octadecatriene, 3.375 mg (3Z,9Z,6R,7S)-6,7-epoxy-octadecadiene and 0.375 mg (3Z,6Z,9S,10R)-9,10-epoxy-octadecadiene were dissolved in n-hexane, the obtained solution was added dropwise to a rubber septum, and after the solvent was volatilized, the sex pheromone lure was obtained.

Embodiment 21: 1.25 mg (3Z,6Z,9Z)-octadecatriene, 1.875 mg (3Z,9Z,6R,7S)-6,7-epoxy-octadecadiene and 1.875 mg (3Z,6Z,9S,10R)-9,10-epoxy-octadecadiene were dissolved in n-hexane, the obtained solution was added dropwise to a rubber septum, and after the solvent was volatilized, the sex pheromone lure was obtained.

Embodiment 22: 1.25 mg (3Z,6Z,9Z)-octadecatriene, 0.375 mg (3Z,9Z,6R,7S)-6,7-epoxy-octadecadiene and 3.375 mg (3Z,6Z,9S,10R)-9,10-epoxy-octadecadiene were dissolved in n-hexane, the obtained solution was added dropwise to a rubber septum, and after the solvent was volatilized, the sex pheromone lure was obtained.

Embodiment 23: 1.25 mg (3Z,6Z,9Z)-octadecatriene, 3.375 mg (3Z,9Z,6R,7S)-6,7-epoxy-octadecadiene and 0.375 mg (3Z,6Z,9R,10S)-9,10-epoxy-octadecadiene were dissolved in n-hexane, the obtained solution was added dropwise to a rubber septum, and after the solvent was volatilized, the sex pheromone lure was obtained.

Embodiment 24: 1.25 mg (3Z,6Z,9Z)-octadecatriene, 1.875 mg (3Z,9Z,6R,7S)-6,7-epoxy-octadecadiene and 1.875 mg (3Z,6Z,9R,10S)-9,10-epoxy-octadecadiene were dissolved in n-hexane, the obtained solution was added dropwise to a rubber septum, and after the solvent was volatilized, the sex pheromone lure was obtained.

Embodiment 25: 1.25 mg (3Z,6Z,9Z)-octadecatriene, 0.375 mg (3Z,9Z,6R,7S)-6,7-epoxy-octadecadiene and 3.375 mg (3Z,6Z,9R,10S)-9,10-epoxy-octadecadiene were dissolved in n-hexane, the obtained solution was added dropwise to a rubber septum, and after the solvent was volatilized, the sex pheromone lure was obtained.

(3) Screening of Binary Octadecadiene Epoxides: A Combination of (3Z,9Z)-6,7-epoxy-octadecadiene and (6Z,9Z)-3,4-epoxy-octadecadiene carbodiene Embodiment 26: 1.25 mg (3Z,6Z,9Z)-octadecatriene, 3.375 mg (3Z,9Z,6S,7R)-6,7-epoxy-octadecadiene and 0.375 mg (6Z,9Z,3R,4S)-3,4-epoxy-octadecadiene were dissolved in n-hexane, and the obtained solution was added dropwise to a rubber septum, and after the solvent was volatilized, the sex pheromone lure was obtained.

Embodiment 27: 1.25 mg (3Z,6Z,9Z)-octadecatriene, 1.875 mg (3Z,9Z,6S,7R)-6,7-epoxy-octadecadiene and 1.875 mg (6Z,9Z,3R,4S)-3,4-epoxy-octadecadiene were dissolved in n-hexane, and the obtained solution was added dropwise to a rubber septum, and after the solvent was volatilized, the sex pheromone lure was obtained.

Embodiment 28: 1.25 mg (3Z,6Z,9Z)-octadecatriene, 0.375 mg (3Z,9Z,6S,7R)-6,7-epoxy-octadecadiene and 3.375 mg (6Z,9Z,3R,4S)-3,4-epoxy-octadecadiene were dissolved in n-hexane, and the obtained solution was added dropwise to a rubber septum, and after the solvent was volatilized, the sex pheromone lure was obtained.

Embodiment 29: 1.25 mg (3Z,6Z,9Z)-octadecatriene, 3.375 mg (3Z,9Z,6S,7R)-6,7-epoxy-octadecadiene and 0.375 mg (6Z,9Z,3S,4R)-3,4-epoxy-octadecadiene were dissolved in n-hexane, and the obtained solution was added dropwise to a rubber septum, and after the solvent was volatilized, the sex pheromone lure was obtained.

Embodiment 30: 1.25 mg (3Z,6Z,9Z)-octadecatriene, 1.875 mg (3Z,9Z,6S,7R)-6,7-epoxy-octadecadiene and 1.875 mg (6Z,9Z,3S,4R)-3,4-epoxy-octadecadiene were dissolved in n-hexane, and the obtained solution was added dropwise to a rubber septum, and after the solvent was volatilized, the sex pheromone lure was obtained.

Embodiment 31: 1.25 mg (3Z,6Z,9Z)-octadecatriene, 0.375 mg (3Z,9Z,6S,7R)-6,7-epoxy-octadecadiene and 3.375 mg (6Z,9Z,3S,4R)-3,4-epoxy-octadecadiene were dissolved in n-hexane, and the obtained solution was added dropwise to a rubber septum, and after the solvent was volatilized, the sex pheromone lure was obtained.

Embodiment 32: 1.25 mg (3Z,6Z,9Z)-octadecatriene, 3.375 mg (3Z,9Z,6R,7S)-6,7-epoxy-octadecadiene and 0.375 mg (6Z,9Z,3R,4S)-3,4-epoxy-octadecadiene were dissolved in n-hexane, and the obtained solution was added dropwise to a rubber septum, and after the solvent was volatilized, the sex pheromone lure was obtained.

Embodiment 33: 1.25 mg (3Z,6Z,9Z)-octadecatriene, 1.875 mg (3Z,9Z,6R,7S)-6,7-epoxy-octadecadiene and 1.875 mg (6Z,9Z,3R,4S)-3,4-epoxy-octadecadiene were dissolved in n-hexane, and the obtained solution was added dropwise to a rubber septum, and after the solvent was volatilized, the sex pheromone lure was obtained.

Embodiment 34: 1.25 mg (3Z,6Z,9Z)-octadecatriene, 0.375 mg (3Z,9Z,6R,7S)-6,7-epoxy-octadecadiene and 3.375 mg (6Z,9Z,3R,4S)-3,4-epoxy-octadecadiene were dissolved in n-hexane, and the obtained solution was added dropwise to a rubber septum, and after the solvent was volatilized, the sex pheromone lure was obtained.

Embodiment 35: 1.25 mg (3Z,6Z,9Z)-octadecatriene, 3.375 mg (3Z,9Z,6R,7S)-6,7-epoxy-octadecadiene and 0.375 mg (6Z,9Z,3S,4R)-3,4-epoxy-octadecadiene were dissolved in n-hexane, and the obtained solution was added dropwise to a rubber septum, and after the solvent was volatilized, the sex pheromone lure was obtained.

Embodiment 36: 1.25 mg (3Z,6Z,9Z)-octadecatriene, 1.875 mg (3Z,9Z,6R,7S)-6,7-epoxy-octadecadiene and 1.875 mg (6Z,9Z,3S,4R)-3,4-epoxy-octadecadiene were dissolved in n-hexane, and the obtained solution was added dropwise to a rubber septum, and after the solvent was volatilized, the sex pheromone lure was obtained.

Embodiment 37: 1.25 mg (3Z,6Z,9Z)-octadecatriene, 0.375 mg (3Z,9Z,6R,7S)-6,7-epoxy-octadecadiene and 3.375 mg (6Z,9Z,3S,4R)-3,4-epoxy-octadecadiene were dissolved in n-hexane, and the obtained solution was added dropwise to a rubber septum, and after the solvent was volatilized, the sex pheromone lure was obtained.

(4) Screening of Binary Octadecadiene Epoxides: A Combination of (6Z,9Z)-3,4-epoxy-octadecadiene and (3Z,6Z)-9,10-epoxy-octadecadiene Embodiment 38: 1.25 mg (3Z,6Z,9Z)-octadecatriene, 3.375 mg (6Z,9Z,3S,4R)-3,4-epoxy-octadecadiene and 0.375 mg (3Z,6Z,9S,10R)-9,10-epoxy-octadecadiene were dissolved in n-hexane, and the obtained solution was added dropwise to a rubber septum, and after the solvent was volatilized, the sex pheromone lure was obtained.

Embodiment 39: 1.25 mg (3Z,6Z,9Z)-octadecatriene, 1.875 mg (6Z,9Z,3S,4R)-3,4-epoxy-octadecadiene and 1.875 mg (3Z,6Z,9S,10R)-9,10-epoxy-octadecadiene were dissolved in n-hexane, and the obtained solution was added dropwise to a rubber septum, and after the solvent was volatilized, the sex pheromone lure was obtained.

Embodiment 40: 1.25 mg (3Z,6Z,9Z)-octadecatriene, 0.375 mg (6Z,9Z,3S,4R)-3,4-epoxy-octadecadiene and 3.375 mg (3Z,6Z,9S,10R)-9,10-epoxy-octadecadiene were dissolved in n-hexane, and the obtained solution was added dropwise to a rubber septum, and after the solvent was volatilized, the sex pheromone lure was obtained.

Embodiment 41: 1.25 mg (3Z,6Z,9Z)-octadecatriene, 3.375 mg (6Z,9Z,3S,4R)-3,4-epoxy-octadecadiene and 0.375 mg (3Z,6Z,9R,10S)-9,10-epoxy-octadecadiene were dissolved in n-hexane, and the obtained solution was added dropwise to a rubber septum, and after the solvent was volatilized, the sex pheromone lure was obtained.

Embodiment 42: 1.25 mg (3Z,6Z,9Z)-octadecatriene, 1.875 mg (6Z,9Z,3S,4R)-3,4-epoxy-octadecadiene and 1.875 mg (3Z,6Z,9R,10S)-9,10-epoxy-octadecadiene were dissolved in n-hexane, and the obtained solution was added dropwise to a rubber septum, and after the solvent was volatilized, the sex pheromone lure was obtained.

Embodiment 43: 1.25 mg (3Z,6Z,9Z)-octadecatriene, 0.375 mg (6Z,9Z,3S,4R)-3,4-epoxy-octadecadiene and 3.375 mg (3Z,6Z,9R,10S)-9,10-epoxy-octadecadiene were dissolved in n-hexane, and the obtained solution was added dropwise to a rubber septum, and after the solvent was volatilized, the sex pheromone lure was obtained.

Embodiment 44: 1.25 mg (3Z,6Z,9Z)-octadecatriene, 3.375 mg (6Z,9Z,3R,4S)-3,4-epoxy-octadecadiene and 0.375 mg (3Z,6Z,9S,10R)-9,10-epoxy-octadecadiene were dissolved in n-hexane, and the obtained solution was added dropwise to a rubber septum, and after the solvent was volatilized, the sex pheromone lure was obtained.

Embodiment 45: 1.25 mg (3Z,6Z,9Z)-octadecatriene, 1.875 mg (6Z,9Z,3R,4S)-3,4-epoxy-octadecadiene and 1.875 mg (3Z,6Z,9S,10R)-9,10-epoxy-octadecadiene were dissolved in n-hexane, and the obtained solution was added dropwise to a rubber septum, and after the solvent was volatilized, the sex pheromone lure was obtained.

Embodiment 46: 1.25 mg (3Z,6Z,9Z)-octadecatriene, 0.375 mg (6Z,9Z,3R,4S)-3,4-epoxy-octadecadiene and 3.375 mg (3Z,6Z,9S,10R)-9,10-epoxy-octadecadiene were dissolved in n-hexane, and the obtained solution was added dropwise to a rubber septum, and after the solvent was volatilized, the sex pheromone lure was obtained.

Embodiment 47: 1.25 mg (3Z,6Z,9Z)-octadecatriene, 3.375 mg (6Z,9Z,3R,4S)-3,4-epoxy-octadecadiene and 0.375 mg (3Z,6Z,9R,10S)-9,10-epoxy-octadecadiene were dissolved in n-hexane, and the obtained solution was added dropwise to a rubber septum, and after the solvent was volatilized, the sex pheromone lure was obtained.

Embodiment 48: 1.25 mg (3Z,6Z,9Z)-octadecatriene, 1.875 mg (6Z,9Z,3R,4S)-3,4-epoxy-octadecadiene and 1.875 mg (3Z,6Z,9R,10S)-9,10-epoxy-octadecadiene were dissolved in n-hexane, and the obtained solution was added dropwise to a rubber septum, and after the solvent was volatilized, the sex pheromone lure was obtained.

Embodiment 49: 1.25 mg (3Z,6Z,9Z)-octadecatriene, 0.375 mg (6Z,9Z,3R,4S)-3,4-epoxy-octadecadiene and 3.375 mg (3Z,6Z,9R,10S)-9,10-epoxy-octadecadiene were dissolved in n-hexane, and the obtained solution was added dropwise to a rubber septum, and after the solvent was volatilized, the sex pheromone lure was obtained.

Embodiment 50: Field trapping tests were carried out at the tea plantation of Jintan Xinpin Tea Industry Co., Ltd., Changzhou City, Jiangsu Province. Sex pheromone lures used in the test were made according to the schemes described in Embodiments 10-49, and a blank control was the lures made of n-hexane. The sex pheromone lures were used with a trap, each treatment process was repeated for 3 times, and the number of trapped insects in one month was counted. The trapping results of Embodiments 10-49 are shown in Table 2.

TABLE 2

| Treatment | Field trapping results of *E. oblique* | |
|---|---|---|
| | Total number of trapped *E. oblique* (Head) | Average number of trapped *E. oblique* (Head/Trap) |
| Blank control | 0 | 0 |
| Embodiment 10 | 92 | 30.7 |
| Embodiment 11 | 122 | 40.7 |
| Embodiment 12 | 183 | 61 |
| Embodiment 13 | 120 | 40 |
| Embodiment 14 | 60 | 20 |
| Embodiment 15 | 24 | 8 |
| Embodiment 16 | 18 | 6 |
| Embodiment 17 | 18 | 6 |
| Embodiment 18 | 33 | 11 |
| Embodiment 19 | 12 | 4 |
| Embodiment 20 | 0 | 0 |
| Embodiment 21 | 0 | 0 |
| Embodiment 22 | 0 | 0 |
| Embodiment 23 | 12 | 4 |
| Embodiment 24 | 32 | 8 |
| Embodiment 25 | 6 | 2 |
| Embodiment 26 | 0 | 0 |
| Embodiment 27 | 0 | 0 |
| Embodiment 28 | 0 | 0 |
| Embodiment 29 | 0 | 0 |
| Embodiment 30 | 0 | 0 |
| Embodiment 31 | 0 | 0 |
| Embodiment 32 | 0 | 0 |
| Embodiment 33 | 0 | 0 |
| Embodiment 34 | 0 | 0 |
| Embodiment 35 | 0 | 0 |
| Embodiment 36 | 0 | 0 |
| Embodiment 37 | 0 | 0 |
| Embodiment 38 | 0 | 0 |
| Embodiment 39 | 0 | 0 |
| Embodiment 40 | 0 | 0 |
| Embodiment 41 | 0 | 0 |
| Embodiment 42 | 0 | 0 |
| Embodiment 43 | 0 | 0 |
| Embodiment 44 | 0 | 0 |
| Embodiment 45 | 0 | 0 |
| Embodiment 46 | 0 | 0 |
| Embodiment 47 | 0 | 0 |
| Embodiment 48 | 0 | 0 |
| Embodiment 49 | 0 | 0 |

The results showed that the trapping effect of the combination of (3Z,9Z,6S,7R)-6,7-epoxy-octadecadiene and (3Z,6Z,9S,10R)-9,10-epoxy-octadecadiene for male *E. oblique* is much better than other combinations, and the trapping effect is the best when the weight ratio of (3Z,9Z,6S,7R)-6,7-epoxy-octadecadiene to (3Z,6Z,9S,10R)-9,10-epoxy-octadecadiene was 2:1. The combination of (3Z,9Z,6S,7R)-6,7-epoxy-octadecadiene and (3Z,6Z,9S,10R)-9,10-epoxy-octadecadiene, compared with (3Z,9Z,6S,7R)-6,7-epoxy-octadecadiene or (3Z,6Z,9S,10R)-9,10-epoxy-octadecadiene alone, can effectively increase the trapping effect on E. oblique, showing synergetic effect with each other.

(5) Screening of Ternary Octadecadiene Epoxides: A Combination of (3Z,9Z,6S,7R)-6,7-epoxy-octadecadiene and (3Z,6Z,9S,10R)-9,10-epoxy-octadecadiene and (6Z,9Z)-3,4-epoxy-octadecadiene Embodiment 51: 1.25 mg (3Z,6Z,9Z)-octadecatriene, 2.5 mg (3Z,9Z,6S,7R)-6,7-epoxy-octadecadiene, 1.25 mg (3Z,6Z,9S,10R)-9,10-epoxy-octadecadiene and 0.19 mg (6Z,9Z,3S,4R)-3,4-epoxy-octadecadiene were dissolved in n-hexane, and the obtained solution was added dropwise to a rubber septum, and after the solvent was volatilized, the sex pheromone lure was obtained.

Embodiment 52: 1.25 mg (3Z,6Z,9Z)-octadecatriene, 2.5 mg (3Z,9Z,6S,7R)-6,7-epoxy-octadecadiene, 1.25 mg (3Z,6Z,9S,10R)-9,10-epoxy-octadecadiene and 0.19 mg (6Z,9Z,3R,4S)-3,4-epoxy-octadecadiene were dissolved in n-hexane, and the obtained solution was added dropwise to a rubber septum, and after the solvent was volatilized, the sex pheromone lure was obtained.

Embodiment 53: Field trapping tests were carried out at the tea plantation of Jintan Xinpin Tea Industry Co., Ltd., Changzhou City, Jiangsu Province. Sex pheromone lures used in the test were made according to the schemes described in Embodiments 51-52, and a blank control was the lures made in Embodiment 12. The sex pheromone lure was used with a trap, each treatment process was repeated 3 times, and the number of trapped insects in one month was counted. The trapping results of Embodiments 51-52 are shown in Table 3.

TABLE 3

Field trapping results of E. oblique

| Treatment | Total number of trapped E. oblique (Head) | Average number of trapped E. oblique (Head/Trap) |
|---|---|---|
| Embodiment 12 | 183 | 61 |
| Embodiment 51 | 121 | 40.3 |
| Embodiment 52 | 108 | 36 |

The results showed that after (6Z,9Z)-3,4-epoxy-octadecadiene was added on the basis of (3Z,9Z,6S,7R)-6,7-epoxy-octadecadiene and (3Z,6Z,9S,10R)-9,10-epoxy-octadecadiene, the trapping effect on E. oblique was not improved. The combination of (3Z,9Z,6S,7R)-6,7-epoxy-octadecadiene and (3Z,6Z,9S,10R)-9,10-epoxy-octadecadiene sex pheromone lures had the best trapping effect.

Trapping Tests of E. oblique and E. grisescens with the High Efficient Sex Pheromone Lures Embodiment 54: Field trapping tests were carried out at the tea plantation of Jintan Xinpin Tea Industry Co., Ltd., Changzhou City, Jiangsu Province. Sex pheromone lures used in the test were made according to the schemes described in Embodiment 12. The sex pheromone lure was used with a trap, each treatment process was repeated for 3 times, and the number of trapped insects in one month was counted. The trapping results of Embodiment 12 are shown in Table 4.

TABLE 4

Field trapping results of E. oblique and E. grisescens

| Treatment | Total number of trapped male pests (Head) | | Average number of trapped male pests (Head/Trap) | |
|---|---|---|---|---|
| | E. oblique | E. grisescens | E. oblique | E. grisescens |
| Embodiment 12 | 183 | 209 | 61 | 69.7 |

The results show that: the high efficient sex pheromone lures corresponding to Embodiment 12 have good trapping effect on E. oblique and E. grisescens, and the effect on E. grisescens is better, which may be related to a high population density of E. grisescens in the tea plantation.

What is claimed is:

1. A highly efficient sex pheromone lure for E. oblique and E. grisescens, wherein the sex pheromone lure is obtained by a process of
dissolving 1.25 mg of (3Z,6Z,9Z)-octadecatriene, 2.5 mg of (3Z,9Z,6S,7R)-6,7-epoxy-octadecadiene and 1.25 mg of (3Z,6Z,9S,10R)-9,10-epoxy-octadecadiene in n-hexane to obtain a solution;
adding the obtained solution dropwise to a rubber septum; and
volatilizing the solvent.

2. The highly efficient sex pheromone lure for E. oblique and E. grisescens according to claim 1, wherein the (3Z,6Z,9S,10R)-9,10-epoxy-octadecadiene is synthesized by the following steps:
(1) synthesizing (2S,3S)-1,2,3-undecanetriol;
(2) synthesizing (2S,3S)-1,2-epoxy-3-p-toluenesulfonate-undecane from the (2S,3S)-1,2,3-undecanetriol;
(3) synthesizing (9S,10R)-9,10-epoxy-octadeca-3,6-diyne from the (2S,3S)-1,2-epoxy-3-p-toluenesulfonate-undecane; and
(4) synthesizing the (3Z,6Z,9S,10R)-9,10-epoxy-octadecadiene.

* * * * *